(12) United States Patent
Hartkens et al.

(10) Patent No.: US 9,795,452 B2
(45) Date of Patent: Oct. 24, 2017

(54) TREATMENT APPARATUS FOR A SUBRETINAL INJECTION AND METHOD FOR ASSISTING IN A SUBRETINAL INJECTION

(71) Applicant: Carl Zeiss Meditec AG, Jena (DE)

(72) Inventors: Thomas Hartkens, Berlin (DE); Abouzar Eslami, Munich (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 15/354,789

(22) Filed: Nov. 17, 2016

(65) Prior Publication Data

US 2017/0135768 A1 May 18, 2017

(30) Foreign Application Priority Data

Nov. 17, 2015 (DE) .......................... 10 2015 119 887

(51) Int. Cl.

| | |
|---|---|
| *A61B 3/10* | (2006.01) |
| *A61F 9/00* | (2006.01) |
| *A61B 34/10* | (2016.01) |
| *A61B 3/13* | (2006.01) |
| *A61B 3/14* | (2006.01) |

(Continued)

(52) U.S. Cl.
CPC .............. *A61B 34/10* (2016.02); *A61B 3/102* (2013.01); *A61B 3/13* (2013.01); *A61B 3/145* (2013.01); *A61F 9/0017* (2013.01); *G06T 7/0012* (2013.01); *G06T 11/003* (2013.01); (Continued)

(58) Field of Classification Search
CPC ........... A61B 3/102; A61B 3/13; A61B 3/145; A61B 34/10; A61B 2034/105; A61B 2034/107; A61F 9/0017; G06T 7/0012; G06T 11/003; G06T 2207/10101
See application file for complete search history.

(56) References Cited

U.S. PATENT DOCUMENTS

| | | | |
|---|---|---|---|
| 8,845,625 B2 * | 9/2014 | Angeley ................. | G06T 7/149 606/6 |
| 9,629,537 B2 * | 4/2017 | Matz ........................ | A61B 3/13 |

(Continued)

OTHER PUBLICATIONS

Fleming, I. N. et al., "Intraoperative Visualization of Anatomical Targets in Retinal Surgery", WACV (pp. 274 to 279), (2008), IEEE Workshop on Applications of Computer Vision.

(Continued)

*Primary Examiner* — Katrina Fujita
(74) *Attorney, Agent, or Firm* — Walter Ottesen, P.A.

(57) ABSTRACT

A treatment apparatus for a subretinal injection into an eye includes a 3D imaging device configured to generate a 3D image of a retina and a choroid of the eye. The apparatus has a planning device for inputting at least one set position for an injection instrument to be used for the injection. The set position is a location indication in the 3D image. The apparatus includes a 2D imaging device to generate a surface image of the retina and supplement the image to form a supplemented image, via the 2D imaging device ascertaining in the surface image at least one location which, in the surface image, corresponds to the at least one set position indicated in the 3D image, and inserting into the surface image at least one mark that corresponds to the ascertained at least one location. A display device displays the supplemented image.

17 Claims, 7 Drawing Sheets

(51) Int. Cl.
  *G06T 7/00*   (2017.01)
  *G06T 11/00*  (2006.01)
(52) U.S. Cl.
  CPC ... *A61B 2034/105* (2016.02); *A61B 2034/107* (2016.02); *G06T 2207/10101* (2013.01)

(56) References Cited

U.S. PATENT DOCUMENTS

2012/0019777 A1    1/2012  Hauger et al.
2014/0160264 A1*   6/2014  Taylor ................. G02B 21/008
                                                    348/79

OTHER PUBLICATIONS

Kreatsoulas, J., "Enhancing Retinal Surgery With Augmented Reality Technology", Retina Today, News Feature, Apr. 2011, pp. 18 to 20.
Martel, J. N. et al, "Subretinal Pneumatic Displacement of Subretinal Hemorrhage", JAMA Ophthalmology, vol. 131, No. 12, Dec. 2013, pp. 1632 to 1635.
Sznitman, R. et al, "Data-Driven Visual Tracking in Retinal Microsurgery", Ayache, N. et al, editor, MICCAI 2012, Part II, LNCS 7511, pp. 568 to 575, 2012, Springer-Verlag, Berlin Heidelberg, Germany.
English translation and Office action of the German Patent Office dated Sep. 12, 2016 in the corresponding German patent application 10 2015 119 887.8.

* cited by examiner

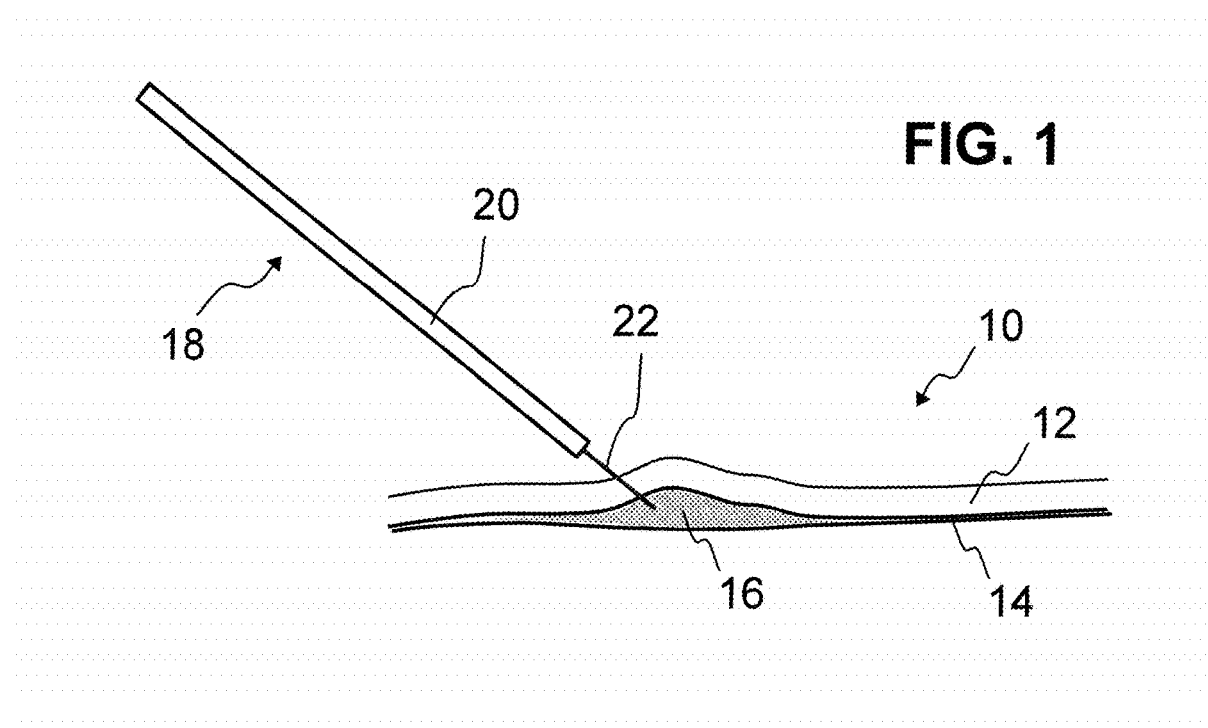
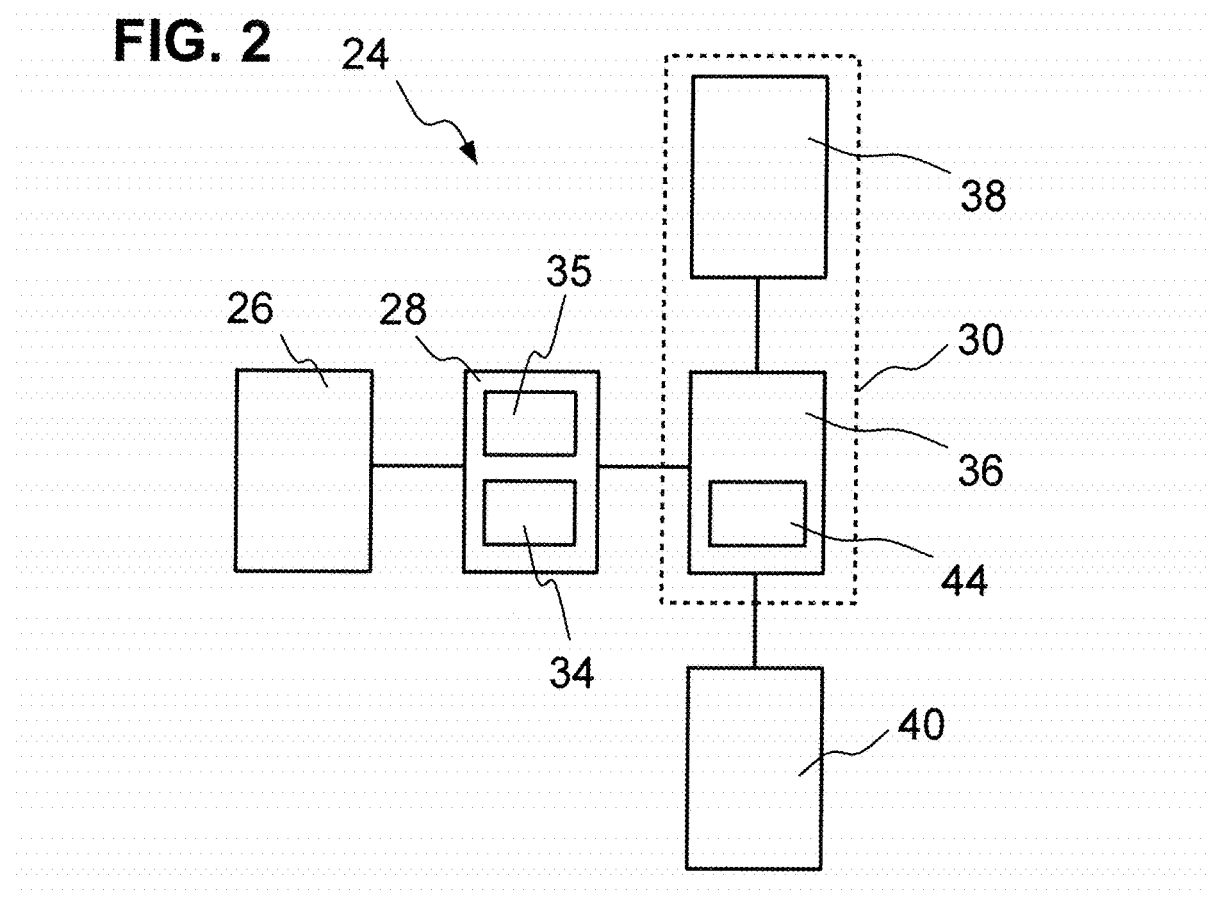

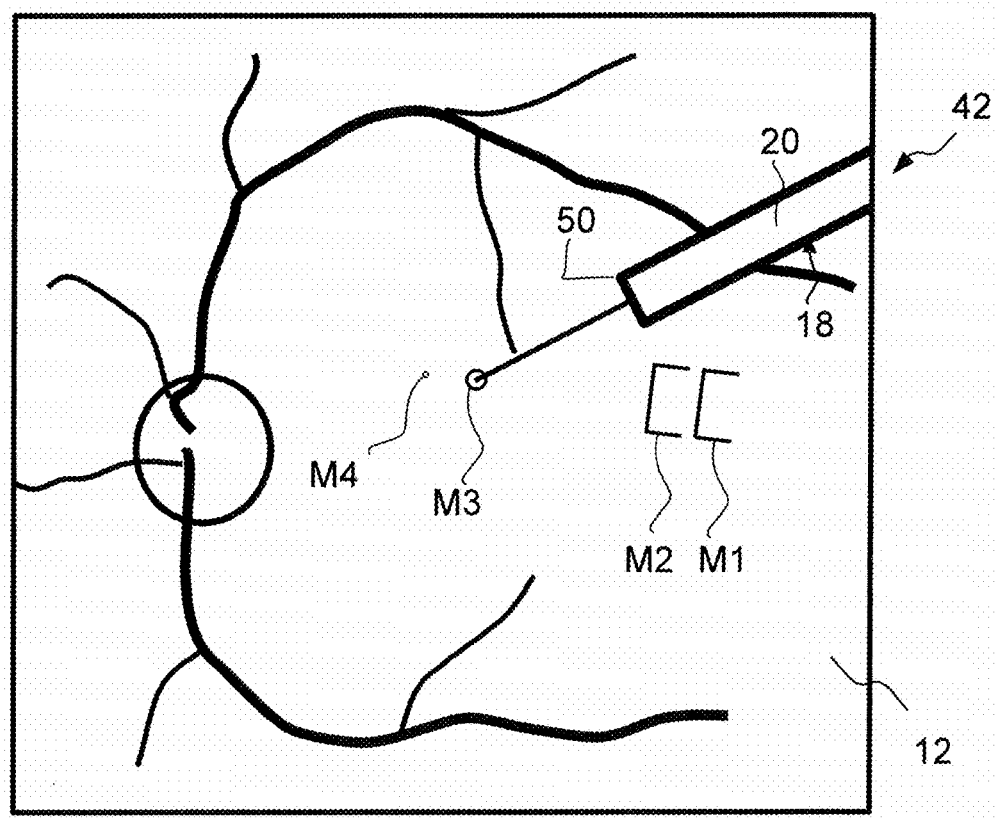

TREATMENT APPARATUS FOR A SUBRETINAL INJECTION AND METHOD FOR ASSISTING IN A SUBRETINAL INJECTION

CROSS REFERENCE TO RELATED APPLICATION

This application claims priority of German patent application no. 10 2015 119 887.8, filed Nov. 17, 2015, the entire content of which is incorporated herein by reference.

FIELD OF THE INVENTION

The invention relates to a treatment apparatus for a subretinal injection into an eye, which includes a 2D imaging device for generating a surface image of the retina. The invention furthermore relates to a method for preparing in the case of a subretinal injection into an eye, which includes the step of imaging the retina and generating a surface image. The invention finally relates to a method for subretinal injection into an eye, which includes the step of imaging the retina and generating a surface image.

BACKGROUND OF THE INVENTION

Submacular hemorrhages are a rare complication in the case of choroidal neovascularization, which frequently leads to a reduction in visual acuity. To treat submacular hemorrhage, injections are made in the subretinal space so as to move the submacular hemorrhage away from the macula, as a result of which the visual acuity in the center of the eye can be retained. Generally, subretinal tissue plasminogen activators and antivascular endothelial growth factors are injected to destroy the blood clot and to liquefy the submacular hemorrhage for mobilization. The injection is illustrated schematically in FIG. 1.

When injecting into the retina, care needs to be made not to inject into the choroid so as to safeguard it against damage. For this reason, injections are carried out preferably where there is sufficient distance between the retina and the choroid. Moreover, subretinal air is introduced to minimize the buoyancy of the liquefied submacular hemorrhage. The injected air furthermore allows the displacement of the submacular hemorrhage. The key to a successful displacement of the submacular hemorrhage is in an understanding of the interaction of various forces which permit the displacement of the liquefied submacular hemorrhage in the subretinal space, and how these forces can be influenced in an appropriate manner.

SUMMARY OF THE INVENTION

It is an object of the invention to increase the treatment success of injections into submacular hemorrhages.

The object can, for example, be achieved by a treatment apparatus for a subretinal injection into an eye. The apparatus includes a 3D imaging device, a planning device, a 2D imaging device and a display device. The 3D imaging device is configured to generate a 3D image of a retina and a choroid of the eye. The planning device is configured for inputting at least one set position for an injection instrument that is to be used for the injection, wherein the at least one set position is a location indication in the 3D image. The 2D imaging device is configured to generate a surface image of the retina and to supplement the latter to form a supplemented surface image, by way of the 2D imaging device ascertaining in the surface image at least one location which, in the surface image, corresponds to the at least one set position indicated in the 3D image, and inserting into the surface image at least one mark that corresponds to the ascertained at least one location. The display device is configured for displaying the supplemented surface image.

The subretinal injection for which the treatment apparatus is preferably provided preferably serves for treating submacular hemorrhages which are present between the retina and the choroid of an eye. In the case of this subretinal injection, in particular a subretinal tissue plasminogen activator and/or an antivascular endothelial growth factor is injected, as described above. This is done preferably using the injection instrument, which has an injection needle (cannula).

In one embodiment, the 3D imaging device at the same time generates a 3D image of the retina and the choroid. Since the submacular hemorrhage is generally located between the retina and the choroid, the 3D imaging device, in one development, images the retina and the choroid together with the submacular hemorrhage, preferably also the size and exact location thereof, in the 3D image. In one embodiment, the 3D imaging device is configured to generate a depth slice image, that is a section through the surface of the retina, the retina and the choroid and the submacular hemorrhage. This is achieved by way of the 3D imaging device generating a 3D image of the relevant tissue.

In one embodiment, the 3D imaging device has a computer and a screen via which the 3D image can be displayed to the surgeon. With preference, and optionally, the 3D imaging device represents the retina, the choroid and the submacular hemorrhage from a plurality of viewing angles such that the surgeon can gain a comprehensive picture of the position and size of the submacular hemorrhage.

In one embodiment, the 3D imaging device and the planning device are arranged to be spatially separate from one another. Optionally, the 3D image is recorded in temporal terms before the set positions are inserted. By way of example, the 3D image is recorded several hours or days before the injection, while the planning of the surgery can take place for example shortly before the injection by way of the insertion of the set positions.

The at least one set position can be inserted into the 3D image with the aid of the planning device. The planning device can, in one embodiment, be realized by way of a computer which displays the 3D image of the 3D imaging device. The surgeon then inserts the at least one set position into the 3D image with the aid of the planning device. The set position can, by way of example, correspond to the location on the retina where the injection is to take place later with the aid of the injection instrument. Optionally, a second or more set positions can be inserted into the 3D image with the aid of the planning device. The second set position can, for example, correspond to the position of the injection instrument at which, after piercing, an injection liquid is intended to be delivered into the submacular hemorrhage. The set positions in particular specify positions of the injection instrument for the planned injection.

It should be highlighted that the planning device itself does not indicate where the individual marks are made, but that the surgeon uses the planning device to mark important steps and/or planned positions of the injection instrument in the 3D image before the actual surgery. He subsequently specifies the set position of the injection instrument for the planned injection in the 3D image.

The coordinates of the set positions are transmitted to the 2D imaging device. They can be transmitted by way of a line connecting the planning device and the 2D imaging device, wirelessly or by data carrier. For example, the coordinates of the set positions can be transmitted from the planning device to the 2D imaging device by way of a data carrier or via the Internet.

The planning device preferably has an input device, via which the set position can be inserted into the 3D image. The input device includes for example a keyboard or a mouse.

The 2D imaging device generates the two-dimensional surface image of the retina. In an embodiment, the surgeon can continuously observe the retina and the injection instrument during surgery using the 2D imaging device. In an embodiment, the 2D imaging device is based on a microscope that is suitable for eye surgeries, as is known from the prior art. The 2D imaging device is also configured for inserting the set position marked in the 3D image as a mark into the surface image which is generated by the 2D imaging device. For calculating the location of the marks, the 2D imaging device in an embodiment projects the coordinates of the set position from the 3D image into the surface image, and in this way ascertains the marks for the positions to be assumed by the injection instrument. The projection of the three-dimensional coordinates of the set position onto the surface image of the retina is preferably done to scale. One or more marks can correspond to the at least one set position.

The set positions of the injection instrument, which are planned before the surgery and are established with the aid of the 3D image of the 3D imaging device, are therefore input into the two-dimensional surface image of the retina and displayed to the surgeon in the thus supplemented surface image.

In an embodiment, the 2D imaging device is configured to generate supplemented live surface images of the retina. Here, the mark that corresponds to the set position is matched to movements or position displacements of the eye and thus of the surface image. Calculation of the location of the mark that corresponds to the set position is continuous in an embodiment.

As compared to subretinal injections, which are carried out exclusively with the aid of a surgical microscope, the treatment apparatus has the advantage that information from a 3D image of the retina and the choroid is taken into consideration in the actual injection. With the surgical microscope, the surgeon only sees the surface of the retina and can thus identify only with difficulty where the submacular hemorrhage is located, which location is suitable for the injection, and/or how deep the injection should be. It is now possible with the aid of the 3D image to establish the injection angle. The surgeon can furthermore plan the injection in advance with the aid of the treatment apparatus and ensure that important steps and/or positions of the injection are displayed during surgery. The surgeon thus has access before and during the actual injection to information gained in advance from the 3D image.

Moreover, it is possible with the aid of the 3D image to visualize the size and arrangement of the submacular hemorrhage between the retina and the choroid. In traditional two-dimensional imaging of the surface of the retina, this information would not be accessible to the surgeon or only with difficulty. Since the surgeon now has access to the information, he will have a better understanding of how the submacular hemorrhage will behave after the injection, that is, after its liquefaction. It is possible in this way to increase the treatment success for subretinal injections.

It is preferred for the 3D imaging device to include an optical coherence tomography scanner. Optical coherence tomography scanners, as are known for example from the prior art, permit reliable generation of a 3D image of the retina and the choroid. The 3D imaging device can additionally include further devices via which 3D images of the retina and the choroid can be obtained.

In an embodiment, the optical coherence tomography scanner is a device which is either integrated in the planning device and/or the 2D imaging device, or is separate from one or both of these devices. In an embodiment, provision is made for the 3D imaging device, in particular the optical coherence tomography scanner, to transmit the 3D image to the stand-alone planning device. This can be done wirelessly, by way of a line, or by data carrier. In an embodiment, the optical coherence tomography scanner is configured such that the 3D image is to scale, that is, the size and position of the submacular hemorrhage are displayed with the aid of the 3D image.

In an embodiment, the treatment apparatus has an injection instrument which includes a shaft and a needle. The shaft has a shaft end at the transition to the needle, and the needle has a needle tip. At least one first set position, which corresponds to the position of the planned puncturing by the needle tip, and a second set position, which corresponds to the deepest position of the needle tip, are insertable into the 3D image on the planning device. The 2D imaging device is configured for inserting the mark for the shaft end, at which the needle tip matches the first set position and/or the second set position, into the surface image.

In an embodiment, the needle is configured in the form of a cannula for placing the injection. The needle tip is preferably the end of the needle by which the injection instrument is inserted into the retina and/or the submacular hemorrhage. By way of example, the shaft represents a connection between the needle and the point of the injection instrument with which the surgeon manages the injection instrument. In an embodiment, the needle is attached to the injection instrument at the shaft end.

The planning device in an embodiment is configured such that at least two set positions can be inserted into the 3D image. The first mark corresponds, for example, to the position on the retina which corresponds to the planned puncture. This position is input by the surgeon on the planning device. The second set position is intended to be at the location that corresponds to the deepest penetration depth of the injection instrument. The injection angle of the injection is specified when two set positions are inserted.

Since the surgeon determines the first and second set positions on the basis of the 3D image of the retina and the choroid, he will have a better understanding of the best puncture location, the puncture angle and the deepest position of the needle tip. In particular, defining the second set position can prevent the choroid from being damaged by the needle tip.

The 2D imaging device in an embodiment inserts those positions of the shaft end at which the needle tip is located at the first set position and/or at the second set position into the surface image in the form of marks. In particular, the shaft end is visible in each case in the supplemented surface image in front of the retina at the positions of the injection instrument which correspond to the first set position and/or the second set position. Specifically, by way of displaying the second mark, the later penetration depth of the injection instrument is controlled exactly such that damage to the choroid is avoided. In particular, the surgeon moves the injection instrument from the indicated first mark for the shaft end, which corresponds to the first set position, to the displayed second mark for the shaft end, which corresponds to the second set position. The display of the marks in the supplemented surface image thus offers assistance to the surgeon in guiding the injection instrument.

The input device can be used to input in particular the length of the needle from the shaft end to the needle tip into the planning device and/or the 2D imaging device to image the marks for the shaft end in the supplemented surface image. Alternatively or additionally, the type of injection instrument can be input, with the length of the needle from the shaft end to the needle tip being stored in a database of the planning device and/or the 2D imaging device with respect to the type of the injection instrument.

In an embodiment, the treatment apparatus furthermore has a position capturing device which is configured to capture the current position of an injection instrument. In that case, the 2D imaging device is configured to display whether the injection instrument is positioned such that the needle tip matches the first set position and/or the second set position.

The position capturing device is implemented in an embodiment in the form of image detection, in particular image detection software. Here, the image detection is configured to detect the injection instrument in the surface image and to determine the position of the injection instrument. Alternatively, the injection instrument can be provided with position capturing marks, which are detected by way of the position capturing device. In this way it is likewise possible for the injection instrument to be detected and for the position of the injection instrument with respect to the retina to be determined.

In one preferred embodiment, the 2D imaging device is configured to display whether the injection instrument is located at the marks which correspond to the set positions that are inserted in the 3D image. As a result, what is displayed in addition to the marks inserted in the surface image, which correspond to the set positions, is whether the injection instrument is located at the locations determined by way of the set positions.

To this end, the injection instrument in an embodiment has a colored boundary in the supplemented surface image, and, if the injection instrument is located at the position corresponding to the set position, is correspondingly highlighted. In an embodiment, the boundary of the injection instrument in the supplemented surface image is blue as long as the injection instrument is not located at the position corresponding to the set position. The boundary changes, for example to green, if the position of the injection instrument corresponds to the set position. The position capturing device offers additional control to the surgeon for moving the injection instrument to the previously established set positions.

What is preferred is for the 2D imaging device to have a microscope and a camera, wherein the 2D imaging device presents the mark corresponding to the set position together with the surface image of the retina on the display device.

In an embodiment, the microscope is a surgical microscope, as is known from the prior art. The display device in an embodiment is a screen, in particular that of a computer, or for example an eyepiece with an integrated display. The 2D imaging device in an embodiment is implemented by a computer. The camera in that case records the surface image of the retina via the microscope and transmits it to the display device. The 2D imaging device in an embodiment is configured to present, in addition to the imaging of the retina and the marks that correspond to the set positions, the injection instrument on the display device.

In an embodiment it is preferred for the treatment apparatus to have a calculation device, which is configured to calculate the size of an internal bleeding and/or to simulate the effect of the injection to be made, in particular in dependence on the position of the puncture, on the internal bleeding.

The calculation device can be implemented for example by software which is installed on a computer, for example the computer of the planning device and/or of the 2D imaging device.

If the 3D imaging device in an embodiment is configured to image the retina, the choroid and a submacular hemorrhage to scale, the calculation device can capture the size of the internal bleeding, in particular the volume thereof. The calculation device to this end determines for example numerous surface points in the 3D image of the submacular hemorrhage. The calculation device in particular uses methods known from the prior art for calculating objects in a three-dimensional image.

Moreover, the calculation device in an embodiment is configured to simulate the effect of the injection to be made. This is done for example by way of a simulation, in which the calculation is based for example on finite elements. In an embodiment, the simulation is based on previously stored data with respect to the behavior of the internal bleeding. In an embodiment, the simulation simulates a movement of the internal bleeding on the basis of the position of the puncture, the injection quantity, the injected substance, the size and arrangement of the submacular hemorrhage between the retina and the choroid.

In an embodiment, the surgeon is thus assisted with respect to the behavior of the submacular hemorrhage after the injection. It should be noted that the calculation device does not make the decisions on behalf of the surgeon, since it is the surgeon who ultimately decides each detail with respect to the injection, such as in particular the position of the puncture, the penetration depth and the injection quantity. However, the calculation device can assist him with the way in which the internal bleeding behaves after the injection. For example, the surgeon can play out various scenarios in dependence on the above-mentioned parameters and determine the correct parameters for the injection depending on the outcome and on his experience.

In another embodiment, the calculation device automatically calculates the at least one set position and thus implements the input of the set position(s).

The invention furthermore relates to a method for preparing a subretinal injection into an eye, including the steps (A) generating a 3D image of a retina and a choroid of the eye, (B) inputting at least one set position of an injection instrument which is to be used for the injection, wherein the at least one set position is a location indication in the 3D image, (C) imaging the retina and generating a surface image of the retina, (D) ascertaining at least one location which in the surface image corresponds to the at least one set position indicated in the 3D image, (E) generating a supplemented surface image by inserting at least one mark into the surface image at the ascertained at least one location, and (F) displaying the supplemented surface image of the retina to assist a surgeon in making the subretinal injection.

The method has the advantages and effects described with respect to the treatment apparatus. In an embodiment, the method provides assistance to the surgeon, that is, it does not then make the decisions to be made with respect to the injection on behalf of the surgeon, but assists him during the preparation of the injection.

What is preferred is that the puncture position of the injection instrument into the retina and/or the injection position and/or the angle of the injection into the retina are input as the set position. Alternatively, as mentioned above, the set positions are determined automatically.

The corresponding position of the injection instrument is displayed, corresponding to the marked set position, by way of (a) mark(s) in the surface image.

In an embodiment it is preferred for the current position of the injection instrument to be captured, wherein it is displayed whether the injection instrument is located at the location corresponding to the set position.

In an embodiment it is preferred for the display of the set position in the supplemented surface image to be carried out by way of projecting the three-dimensional set position of the injection instrument onto a two-dimensional plane of the surface image.

In an embodiment it is preferred for the size of an internal bleeding to be calculated via a calculation device, and/or for the effect of the injection to be made to be simulated to the internal bleeding, in particular in dependence on the position of the puncture. The calculation device optionally also calculates the set position.

In an embodiment it is preferred for the steps (C) to (F) to be repeated, in particular more than once, for providing a supplemented live surface image. As a result, in particular the location of the mark changes if the eye moves. The mark is thus preferably matched to the position of the eye.

The invention furthermore relates to a method for subretinal injection into an eye, including the steps (a) generating a 3D image of a retina and a choroid of the eye, (b) inputting at least one set position of an injection instrument which is to be used for the injection, wherein the at least one set position is a location indication in the 3D image, (c) imaging the retina and generating a surface image of the retina, (d) ascertaining at least one location which in the surface image corresponds to the at least one set position indicated in the 3D image, (e) generating a supplemented surface image by inserting at least one mark into the surface image at the ascertained at least one location, and (f) displaying the supplemented surface image of the retina during the subretinal injection.

In particular, the method has the advantages and effects described with respect to the treatment apparatus and the method described above.

What is preferred is that the steps (c) to (f) are repeated multiple times for providing a supplemented live surface image.

The abovementioned embodiments can of course also be combined.

BRIEF DESCRIPTION OF THE DRAWINGS

The invention will now be described with reference to the drawings wherein:

FIG. 1 shows an injection for treating a submacular hemorrhage according to the prior art;

FIG. 2 shows the schematic setup of a treatment apparatus;

DESCRIPTION OF THE PREFERRED EMBODIMENTS OF THE INVENTION

Figure 3A:
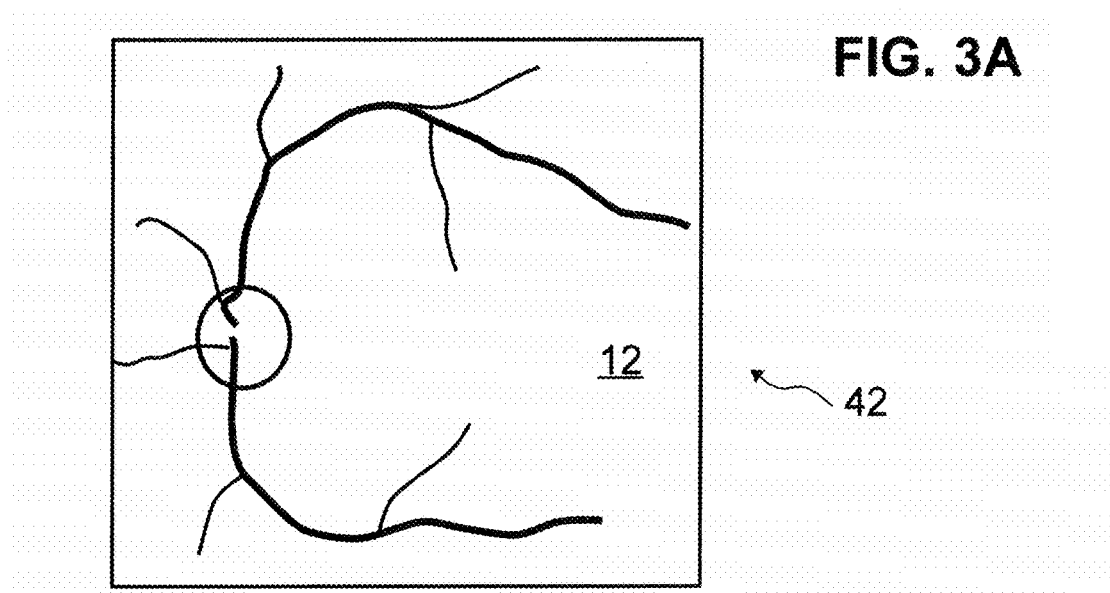
FIG. 3A shows the surface image of a retina via a 2D imaging device of the treatment apparatus.

FIG. 1 shows a cross section of the ocular fundus of an eye 10. Specifically, the retina 12 and the choroid 14 are illustrated in cross section. A submacular hemorrhage 16 is located between the retina 12 and the choroid 14. To treat the submacular hemorrhage 16, a substance, for example a tissue plasminogen activator and an antivascular endothelial growth factor, is injected into the submacular hemorrhage 16 with the aid of an injection instrument 18. The injection instrument 18 has a shaft 20 and a needle 22. During the injection, the needle 22 of the injection instrument 18 penetrates into the submacular hemorrhage 16 and injects the substance so as to liquefy the submacular hemorrhage 16.

FIG. 2 shows the schematic setup of a treatment apparatus 24, which includes a 3D imaging device 26, a planning device 28, a 2D imaging device 30, and a display device 40. The 3D imaging device 26 is configured as an optical coherence tomography scanner and can present the retina 12, the choroid 14 and the submacular hemorrhage 16 in a 3D image 32.

The planning device 28 has a calculation device 34 and an input device 35. The 3D imaging device 26 transmits the 3D image 32 to the planning device 28 via an electric line. The surgeon can indicate set positions S1, S2 in the 3D image 32 via the planning device 28 and the input device 35, as will be explained below. The input device 35 includes a keyboard and a mouse.

The calculation device 34 determines the size and position of the submacular hemorrhage 16 to scale. The calculation device 34 in particular captures the volume of the submacular hemorrhage 16. This can optionally be used to determine the quantity of the substance that is to be injected.

The calculation device 34 is optionally furthermore configured to simulate the behavior of the submacular hemorrhage 16 after the injection. In particular, the calculation device 34 then simulates the movement of the submacular hemorrhage 16 after it has been liquefied by the injection of the substance. To this end, the calculation device 34 uses a simulation method, for example according to the finite element method. The planning device 28 and the calculation device 34 can be implemented on a computer 36 by way of a software program.

The 2D imaging device 30 includes a computer 36 and a microscope 38 with a camera system. The microscope 38 continuously generates a surface image 42 of the retina 12; this produces a live surface image. The image signal of the surface image is transmitted to the computer 36, which supplements the surface image with marks M1, M2, M3, M4, which correspond to the set positions S1, S2, and thus generates a supplemented surface image 42, which it transmits to the display device 40. This process will be described below. The display device 40 is an eyepiece or a screen, in or on which the surface image 42 and the marks M1, M2, M3, M4 are displayed.

A position capturing device 44 is also implemented by the computer 36. The position capturing device 44 detects the injection instrument 18 in the surface image 42 and determines the position of the injection instrument 18 with respect to the retina 12. In the present case, this is done by way of image detection software. The position capturing device 44 indicates to the surgeon whether the injection instrument 18 is arranged at the marks M1, M2, M3, M4, which correspond to the set positions S1, S2. This will be explained below.

Figure 3B:
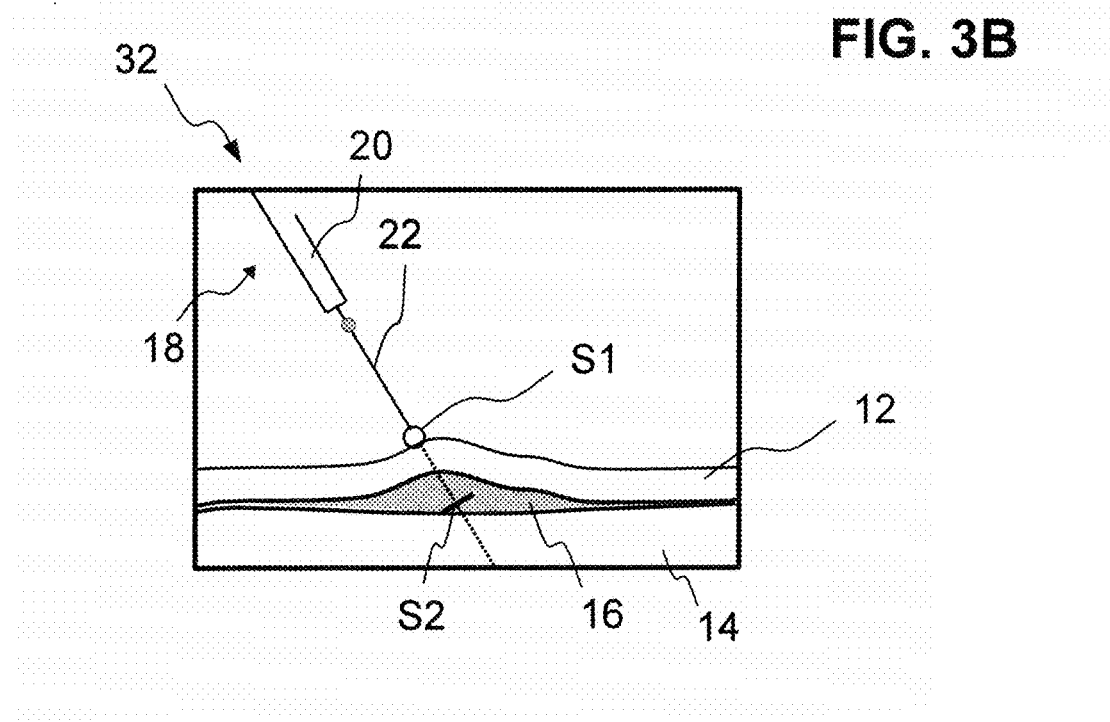
FIG. 3B shows a cross section of a 3D image of the retina and the choroid.

FIG. 3A shows a surface image of the retina 12, which was recorded by the 2D imaging device 30. A position of the submacular hemorrhage 16 and in particular the size thereof is difficult to see on the surface image 42. For this reason, the 3D imaging device 26 is used to record in advance a 3D image 32 of the retina 12 and of the choroid 14 and of the submacular hemorrhage 16. A cross section of such a 3D image 32 is illustrated in FIG. 3B. This clearly shows the size, the shape and the position of the submacular hemorrhage 16.

The planning device 28 additionally forms a representation of the injection instrument 18 in the cross section of the 3D image 32 so as to facilitate insertion of corresponding positions of the injection instrument 18 by way of set positions S1, S2 in the cross section of the 3D image 32. A first set position S1 corresponds to the location on the retina 12, at which the needle 22 of the injection instrument 18 is intended to penetrate into the retina 12. A second set position S2 corresponds to the position of the deepest penetration of the needle 22. The set positions S1, S2 are specified by the surgeon or by the computer, and the planning device 28 calculates the coordinates of the set positions S1, S2 in the 3D image 32.

Figure 4:
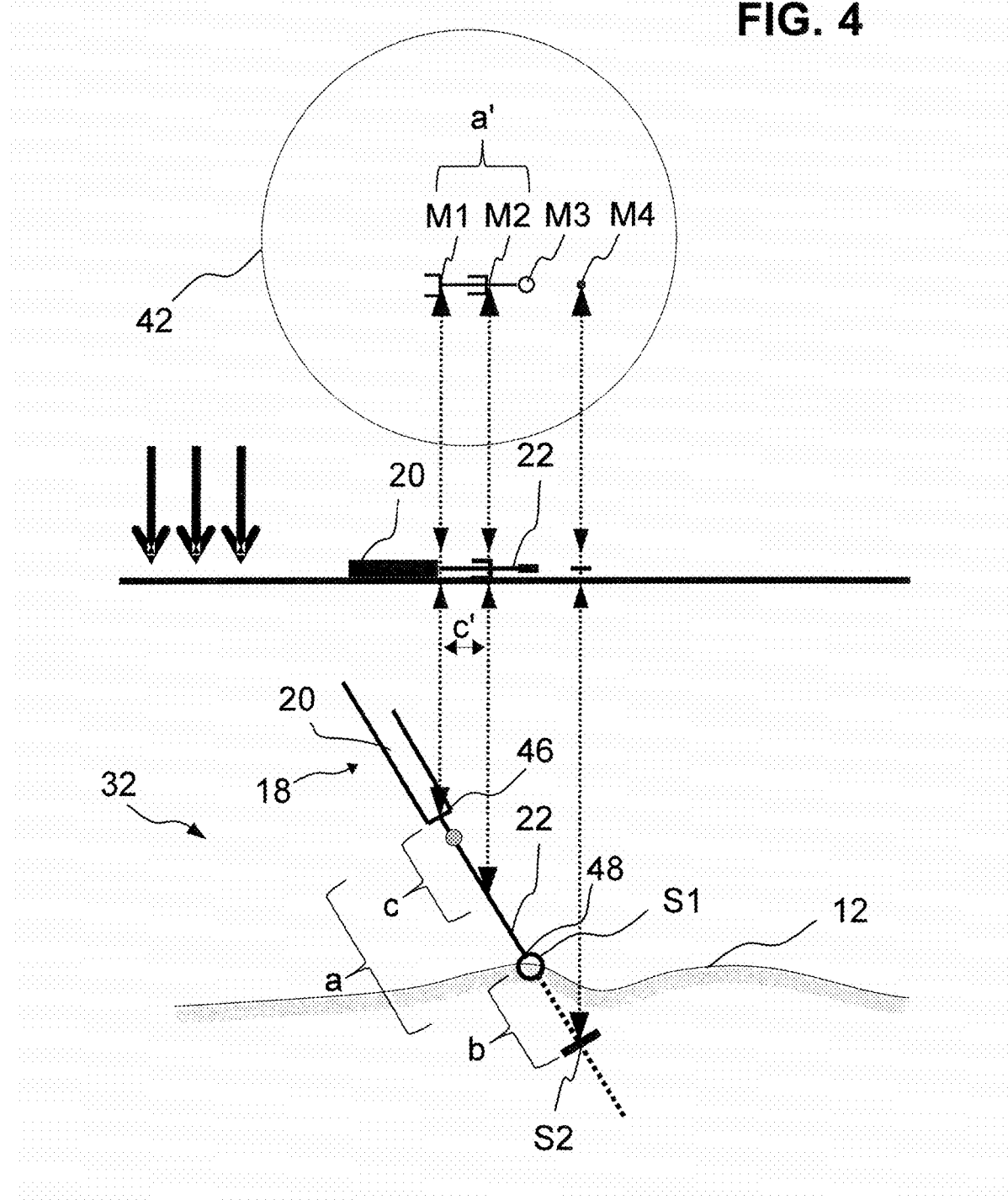
FIG. 4 shows a schematic illustration of the mode of operation of the treatment apparatus.

FIG. 4 schematically illustrates the mode of operation of the planning device 28 and of the 2D imaging device 30. The lower part of FIG. 4 illustrates a cross section of the 3D image 32. The planning device 28 here schematically illustrates the injection instrument 18.

The injection instrument 18 has a shaft end 46, which corresponds to the transition between the shaft 20 and the needle 22. The needle 22 furthermore has a needle tip 48. A length a of the needle 22 from the shaft end 46 to the needle tip 48 is known to the planning device 28, for example because it was input by the surgeon via the input device 35.

Using the 3D image 32 (and optionally utilizing information provided by the calculation device 34), the surgeon specifies the first set position S1, which corresponds to the puncture location of the needle 22, and the second set position S2, which corresponds to the location of the deepest penetration of the needle 22 and to the location of the injection to be made. On the basis of the two set positions S1, S2, the injection angle and a path length b of penetration into the submacular hemorrhage 16 are also obtained.

The path length b corresponds to a movement of the injection instrument 18, which can be tracked by way of the movement of the shaft end 46. The subretinal movement of the needle tip 48 itself cannot be tracked with the aid of the live surface image 42. The presentation of the injection instrument 18 above the retina 12 in the 3D image 32 is now projected onto the imaging plane of the surface image, as is illustrated in the center of FIG. 4. The needle 22 now no longer has the length a in the two-dimensional projection into the plane of the surface image, but a length a'. Moreover, the movement of the shaft end 46 that is visible in the surface image now no longer corresponds to a path length c, but, owing to the projection, to a path length c'.

For the supplemented surface image 42, this gives three marks M1, M2, M3. Mark M1 is assigned to the shaft end 46, when the needle tip 48 is located at the mark M3, which corresponds to the first set position S1 in the 3D image 32. The set positions S1, S2 determine the injection angle of the injection instrument 18. In a non-supplemented two-dimensional surface image 42 of the retina 12, that is, without the display of the marks M1 and M3, the correct injection angle can be assumed only with difficulty.

If the needle tip 48 is located at the mark M3, and the shaft end 46 at the mark M1, the injection angle is correct. With this preparation, the surgeon guides the shaft end 46 of the injection instrument 18 from the mark M1 to the mark M2. Consequently, the needle tip 48 moves from the mark M3 to the mark M4, which is inserted only virtually, since the needle tip 48 is not visible subretinally in the surface image. Therefore, the previously marked penetration depth is displayed to the surgeon with the aid of marks M1 and M2, specifically via the movement of the shaft end 46.

Figure 5A:
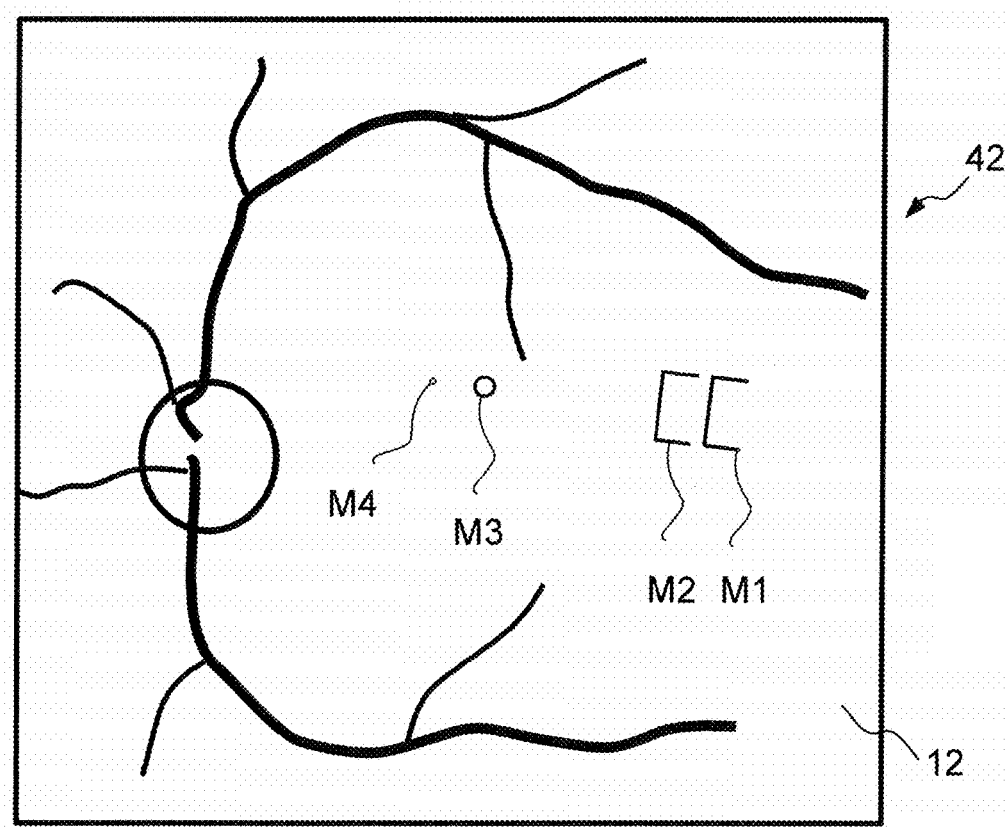
FIG. 5A shows a supplemented surface image of the retina.
Figure 5B:
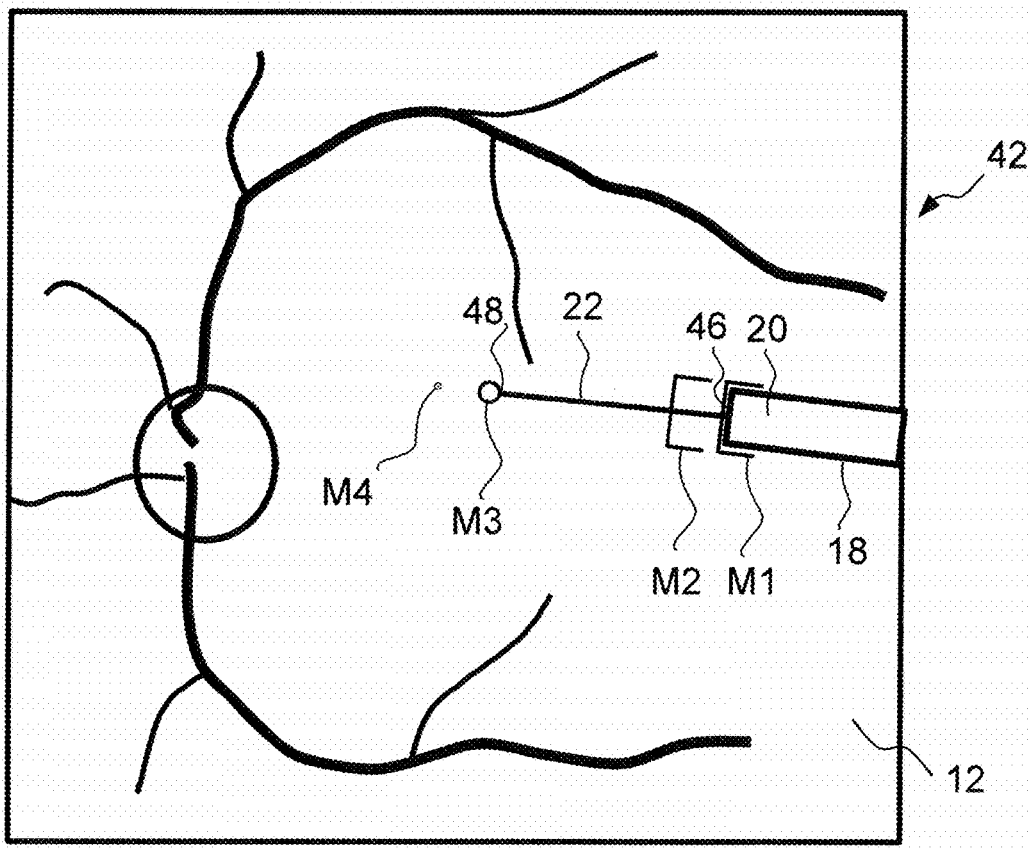
FIG. 5B shows a supplemented surface image of the retina with an injection instrument at the puncture location.

FIG. 5A shows the supplemented surface image 42 of the retina 12. FIG. 5B shows the supplemented surface image 42 of the retina 12, at which the injection instrument 18 is located above the retina 12. In particular, the needle tip 48 is arranged at the puncture location which corresponds to the mark M3. The marks M1 and M2 are illustrated in the supplemented surface image 42 by the 2D imaging device 30 in the form of differently drawn parentheses. In the illustration shown in FIG. 5B, the shaft end 46 and the needle tip 48 are arranged such that they match the marks M1 and M3. This ensures that the injection angle is correct.

Figure 6:
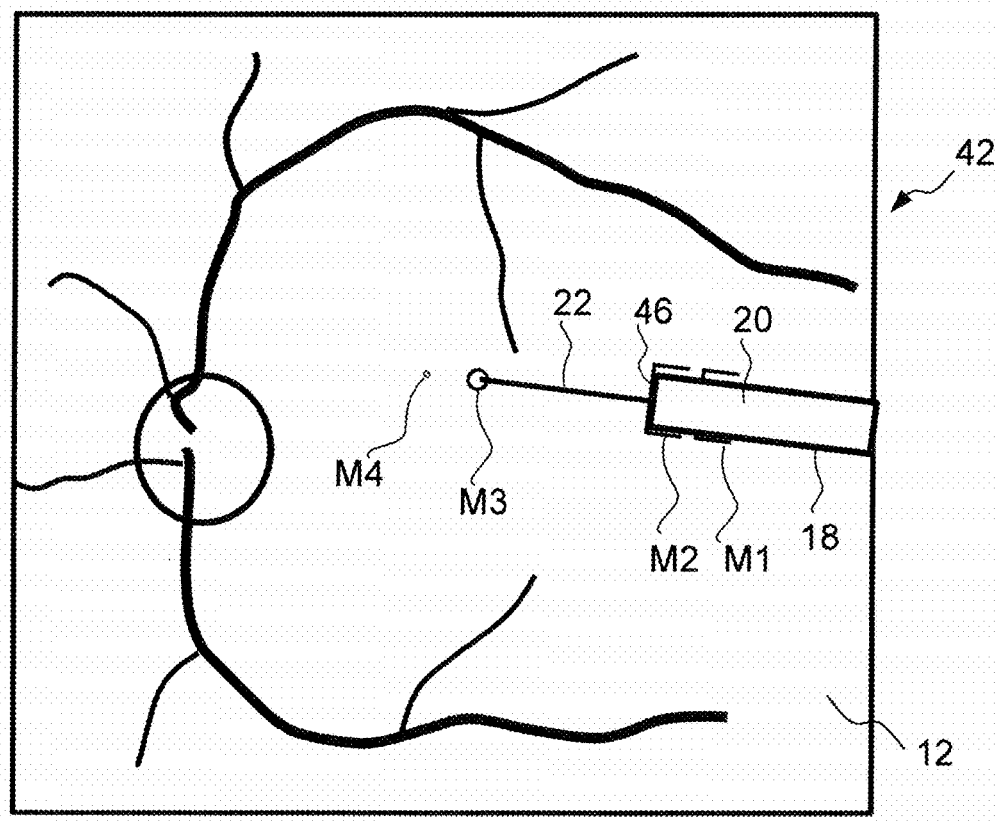
FIG. 6 shows a supplemented surface image of the retina with an injection instrument which has penetrated into the retina; and, FIG. 7 shows a supplemented surface image of the retina, in which the injection instrument is displayed by way of a position capturing device.

In order to now actually penetrate into the retina 12, the injection instrument 18 is moved in terms of its shaft end 46 from the mark M1 to the mark M2, as is illustrated in FIG. 6. With this movement, the needle tip 48 moves from the puncture location at the mark M3 to the deepest penetration depth at the mark M4, which corresponds to the second set position S2 in the 3D image 32. Since the needle tip 48 has now penetrated into the retina 12, it is no longer visible in the surface image 42 of FIG. 6. With this movement of the shaft end 46 from the mark M1 to the mark M2, the surgeon can ensure that the injection angle remains unvaried.

FIG. 7 additionally shows a boundary 50 of the shaft 20 of the injection instrument 18 in the supplemented surface image 42. The position of the injection instrument 18 is captured with the aid of the position capturing device 44. The 2D imaging device 30 calculates, starting with the set positions S1, S2, the corresponding marks M1 to M4 of the injection instrument 18. If the injection instrument 18 is not located at one of the marks M1 to M4, the boundary 50 is shown in color, for example in blue. If the position of the injection instrument 18 matches one of the marks M1 to M4, the color of the boundary 50 changes, for example from blue to green. This serves as an additional aid for the surgeon to position the injection instrument 18 correctly.

It is understood that the foregoing description is that of the preferred embodiments of the invention and that various changes and modifications may be made thereto without departing from the spirit and scope of the invention as defined in the appended claims.

What is claimed is:

1. A treatment apparatus for a subretinal injection into an eye, the treatment apparatus comprising:
  a three-dimensional imaging device configured to generate a three-dimensional image of a retina and a choroid of the eye;
  a planning device configured for inputting at least one set position (S1, S2) for an injection instrument that is to be used for injection;
  said at least one set position (S1, S2) being a location indication in said three-dimensional image;
  a two-dimensional imaging device configured to generate a surface image of the retina;
  said two-dimensional imaging device being further configured to ascertain in said surface image at least one location which in said surface image corresponds to said at least one set position (S1, S2) indicated in said three-dimensional image;
  said two-dimensional imaging device being further configured to insert into said surface image at least one mark corresponding to said at least one location ascertained so as to form a supplemented surface image; and,
  a display device configured to display said supplemented surface image.

2. The treatment apparatus of claim 1, wherein said three-dimensional imaging device includes an optical coherence tomography scanner.

3. The treatment apparatus of claim 1, wherein:
  said injection instrument includes a shaft and a needle;
  said shaft has a shaft end whereat said injection device transitions from said shaft to said needle;
  said needle has a needle tip;
  said at least one set position (S1, S2) includes a first set position (S1) corresponding to a position of a planned puncturing by said needle tip and a second set position (S2) corresponding to a deepest position of said needle tip;
  said planning device is configured to insert said first set position (S1) which corresponds to a position of a planned puncturing by said needle tip and to insert said second set position (S2);
  said at least one mark including a first mark for said shaft end at which said needle tip matches said first set position (S1) and a second mark for said shaft end at which said needle tip matches said second set position (S2); and,
  said two-dimensional imaging device being further configured to insert at least one of said first mark and said second mark into said surface image.

4. The treatment apparatus of claim 3 further comprising:
  a positioning device configured to capture a current position of said injection instrument; and,
  said two-dimensional imaging device being further configured to display whether said injection instrument is positioned such that the position of said needle tip matches at least one of said first set position and said second set position.

5. The treatment apparatus of claim 1, wherein:
  said three-dimensional imaging device includes a microscope and a camera; and,
  said two-dimensional imaging device is configured to represent said at least one mark corresponding to said at least one set position (S1, S2) together with said surface image of the retina on said display device.

6. The treatment apparatus of claim 1 further comprising a calculation device configured to at least one of calculate a size of an internal bleeding and to simulate an effect of an injection to be made on the internal bleeding.

7. The treatment apparatus of claim 1 further comprising a calculation device configured to at least one of calculate a size of an internal bleeding and to simulate an effect of an injection to be made on the internal bleeding in dependence upon a position of a puncture.

8. A method for preparing a subretinal injection in an eye, the method comprising the steps of:
  (a) generating a three-dimensional image of a retina and a choroid of the eye;
  (b) inputting at least one set position of an injection instrument to be used for the injection, wherein the at least one set position is a location indication in the three-dimensional image;
  (c) imaging the retina and generating a surface image of the retina;
  (d) ascertaining at least one location which in the surface image corresponds to the at least one set position indicated in the three-dimensional image;
  (e) generating a supplemented surface image by inserting at least one mark into the surface image at the ascertained at least one location; and,
  (f) displaying the supplemented surface image of the retina to assist a surgeon in making the subretinal injection.

9. The method of claim 8, wherein at least one of a puncture position of the injection instrument into the retina, an injection position, and an angle of an injection into the retina are input as the at least one set position.

10. The method of claim 9, wherein a corresponding position of the injection instrument is displayed via said at least one mark in the supplemented surface image corresponding to the marked set position.

11. The method of claim 8 further comprising the step of:
  capturing the current position of the injection instrument; and,
  displaying whether the injection instrument is positioned at a location corresponding to the at least one set position.

12. The method of claim 8 further comprising the step of projecting the three-dimensional set position into a two-dimensional plane so as to effect the displaying of the set position in the surface image.

13. The method of claim 8 further comprising at least one of calculating at least one of the size of an internal bleeding via a calculation device and simulating an effect of an injection to be made on the internal bleeding via a calculation device.

14. The method of claim 13, wherein the effect of an injection to be made on the internal bleeding is simulated in dependence upon the position of the puncture.

15. The method of claim 8, wherein said steps (c) to (f) are repeated.

16. A method for a subretinal injection in an eye, the method comprising the steps of:
  (a) generating a three-dimensional image of a retina and a choroid of the eye;
  (b) inputting at least one set position of an injection instrument to be used for the injection, wherein the at least one set position is a location indication in the three-dimensional image;
  (c) imaging the retina and generating a surface image of the retina;
  (d) ascertaining at least one location which in the surface image corresponds to the at least one set position indicated in the three-dimensional image;

(e) generating a supplemented surface image by inserting at least one mark into the surface image at the ascertained at least one location; and,
(f) displaying the supplemented surface image of the retina during the subretinal injection.

17. The method of claim 16, wherein said steps (c) to (f) are repeated.

* * * * *